(12) United States Patent
Higgins

(10) Patent No.: US 6,168,430 B1
(45) Date of Patent: Jan. 2, 2001

(54) ORTHODONTIC APPLIANCE FOR TREATING OVERJET

(76) Inventor: Duncan Higgins, 203 - 7313 120$^{th}$Street, Delta, British Columbia (CA), V4C 6P5

( * ) Notice: Under 35 U.S.C. 154(b), the term of this patent shall be extended for 0 days.

(21) Appl. No.: 09/455,321

(22) Filed: Dec. 6, 1999

(51) Int. Cl.$^7$ ..................................................... A61C 3/00
(52) U.S. Cl. ................................................ 433/19; 433/7
(58) Field of Search .................................. 433/19, 7, 18, 433/20, 22

(56) References Cited

U.S. PATENT DOCUMENTS

| | | | |
|---|---|---|---|
| 2,959,856 | 11/1960 | Gurin | 433/22 |
| 4,462,800 | 7/1984 | Jones | 433/19 |
| 4,618,324 | * 10/1986 | Nord | 433/19 |
| 4,707,646 | 11/1987 | Jasper | 433/19 |
| 4,708,648 | 11/1987 | Weissman | 433/49 |
| 5,697,781 | * 12/1997 | Ellingson | 433/19 |
| 5,711,667 | 1/1998 | Vogt | 433/19 |

OTHER PUBLICATIONS

Journal of Clinical Orthodontics, S. Jay Bowman, DMD, MSD, Class II Combination Therapy, vol. XXXII No. 10, Oct. 1998, p. 613.

* cited by examiner

Primary Examiner—John J. Wilson
(74) Attorney, Agent, or Firm—Norman M. Cameron

(57) ABSTRACT

An orthodontic appliance is adapted for treating overjet in a patient having an upper jaw, a lower jaw, lower teeth in the lower jaw and upper teeth in the upper jaw which are abnormally forward of the lower teeth. The teeth have lingual sides and labial sides. The appliance includes an upper attachment device which is configured to be secured to at least one of the upper teeth on each side of the upper jaw. A lower attachment device has a pair of lower connectors. Each lower connector is configured to be secured to at least one of the lower teeth of the patient on each side of the lower jaw. A rigid, wire-like lingual bow is extendable between the lower connectors about the lingual sides of the lower teeth. A rigid, wire-like labial bow is extendable between the lower connectors about the labial sides of the lower teeth. The bows are connected to the lower connectors. A bite jumping device interconnects each side of the upper attachment device to a corresponding side of the lower attachment device. Each bite jumping device includes a first connector for connecting to the upper attachment device, a second connector for connecting to the lower attachment device and a biasing member which biases the lower attachment device forwardly with respect to the upper attachment device.

15 Claims, 5 Drawing Sheets

ORTHODONTIC APPLIANCE FOR TREATING OVERJET

BACKGROUND OF THE INVENTION

This invention relates to orthodontic appliances and, in particular, to orthodontic appliances for treating overjet in patients.

Dental overjet or overbite refers to a condition where a greater than normal horizontal gap exists between the upper and lower front teeth, due to proclination or flaring of the upper front teeth, or a deficient lowerjaw. Typical treatments fall into several categories. The first is retracting or pushing back the upper teeth. A second is proclining or pushing forward the lower teeth. A further treatment is surgical lengthening of the lowerjaw. Another treatment is orthopedic correction whereby forces on the teeth are transmitted to the jaws of growing children.

The term Bite Jumping is normally used to describe appliances that contact the teeth and hold the lower jaw forward, causing stretching of the muscles surrounding the lower jaw. The stretched muscles supply a force acting on the teeth and jaws to pull the upper teeth back, push the lower teeth forward, inhibit the upperjaw from growing forward and encourage the lower jaw to grow forward.

Bite Jumping appliances can be removable or nonremovable or fixed to the teeth by orthodontic bands or crowns and dental cement.

The Herbst appliance is an example of a fixed appliance. It uses rods and tubes to hold the lower jaw forward and places force on the teeth and jaws through stretched muscles.

The Jasper jumper is a spring which connects to braces to push the upper teeth back and the lower teeth forward. In the past it has been used in the permanent dentition with full braces on the upper and lower teeth.

Bite jumping appliances are used by some orthodontists on young patients with mixed dentition where baby and adult teeth are present. The appliances used are typically of the removable type or the Herbst style fixed type.

U.S. Pat. No. 5,711,667 to Vogt discloses a bite jumping device for treating dental protrusion of the upper teeth relative to the lower teeth. It uses braces on the lower teeth. U.S. Pat. No. 4,708,648 to Jasper discloses a similar device.

U.S. Pat. No. 4,462,800 to Jones discloses an orthodontic bite jumping device having a screw at each end of telescoping members.

SUMMARY OF THE INVENTION

There is provided, according to an embodiment of the invention, an orthodontic appliance for treating overjet in a patient having an upper jaw, a lower jaw, lower teeth in the lower jaw and upper teeth in the upper jaw which are abnormally forward of the lower teeth. The teeth have lingual sides and labial sides. The appliance includes an upper attachment device configured to be secured to at least one of the upper teeth on each side of the upper jaw. A lower attachment device has a pair of lower connectors. Each lower connector is configured to be secured to at least one of the lower teeth of the patient on each side of the lower jaw. A rigid, wire-like lingual bow is extendable between the lower connectors about the lingual sides of the lower teeth. A rigid, wire-like labial bow is extendable between the lower connectors about the labial sides of the lower teeth. The bows are connected to the lower connectors. A bite jumping device interconnects each side of the upper attachment device to a corresponding side of the lower attachment device. Each bite jumping device includes a first connector for connecting to the upper attachment device, a second connector for connecting to the lower attachment device and a biasing member which biases the lower attachment device forwardly with respect to the upper attachment device.

DETAILED DESCRIPTION OF THE PREFERRED EMBODIMENTS

Figure 1:
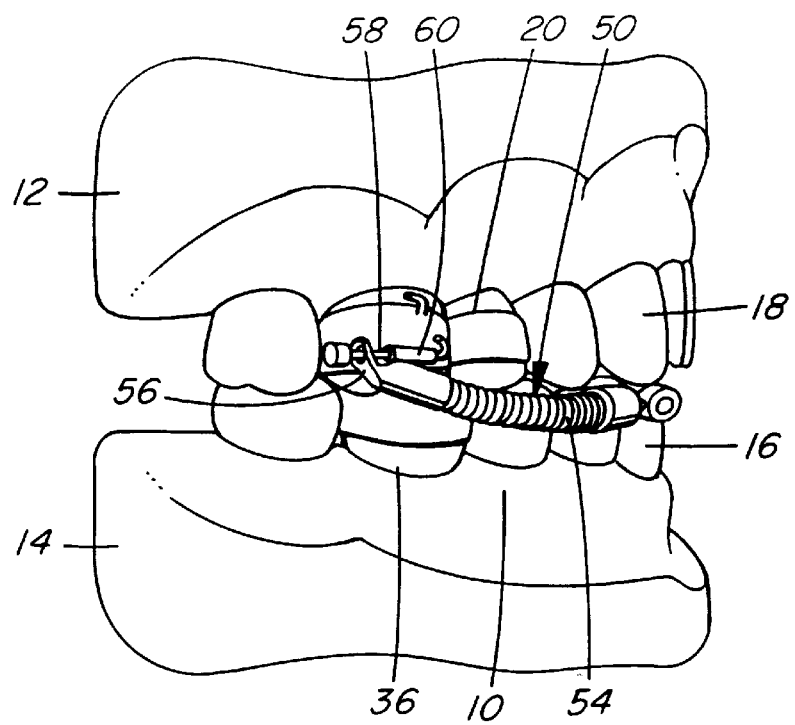
FIG. 1 is a side view of an orthodontic appliance, according to an embodiment of the invention, as viewed from the right side of a patient's mouth, with the patient's jaws closed.

Referring to the drawings, and first to FIGS. 1–6, these show an orthodontic appliance 10 in a patient having an upper jaw 12 and a lower jaw 14. There are lower teeth 16 in the lower jaw and upper teeth 18 in the upper jaw. The appliance corrects a condition where the upper teeth are abnormally forward of the lower teeth.

The appliance includes an upper attachment device 20 configured to be secured to at least one of the upper teeth on each side of the upper jaw. In this example the upper attachment device is a palatal expansion appliance. This embodiment is preferred for younger patients without a full set of permanent teeth. The attachment device is secured either to permanent teeth or temporary teeth which are retained relatively late, or a combination of both. The palatal expansion appliance is known and, therefore, is not described in detail. It includes bands 22 and 24 which extend about two adjacent teeth on each side of the jaw and an arch 25 extending therebetween.

There is a lower attachment device 30 which includes a pair of lower connectors in the form of bands 32 and 34 extending about molars 36 and 38 on opposite sides of the patient's lower jaw. There is a rigid, wire-like lingual bow 40 which extends between the lower connectors about the lingual sides of the lower teeth of the patient. In this example the lingual bow is of 0.045" stainless steel wire. The lingual bow is connected to the lower connectors, in this case by soldering. It may also be connected by tubes similar to the embodiment of FIGS. 7 and 8 described below. The lingual bow in this example has a pair of occlusal rests 42 and 44 which extend over the occlusal surface of the first bicuspid teeth. These help prevent the lingual and labial wires from moving down and impinging on the gum tissue.

The lower attachment device 30 also includes a rigid, wire-like labial bow 46 which extends between the bands 32 and 34 about the labial sides of the lower teeth. This bow is made of stainless-steel wire in this example similar to the lingual bow. The labial bow is also connected to the bands 32 and 34, in this example by soldering. The labial bow bypasses the canine and bicuspid teeth. It contacts the incisor teeth to prevent then from proclining or flaring so much as to open spaces between the teeth.

Figure 2:
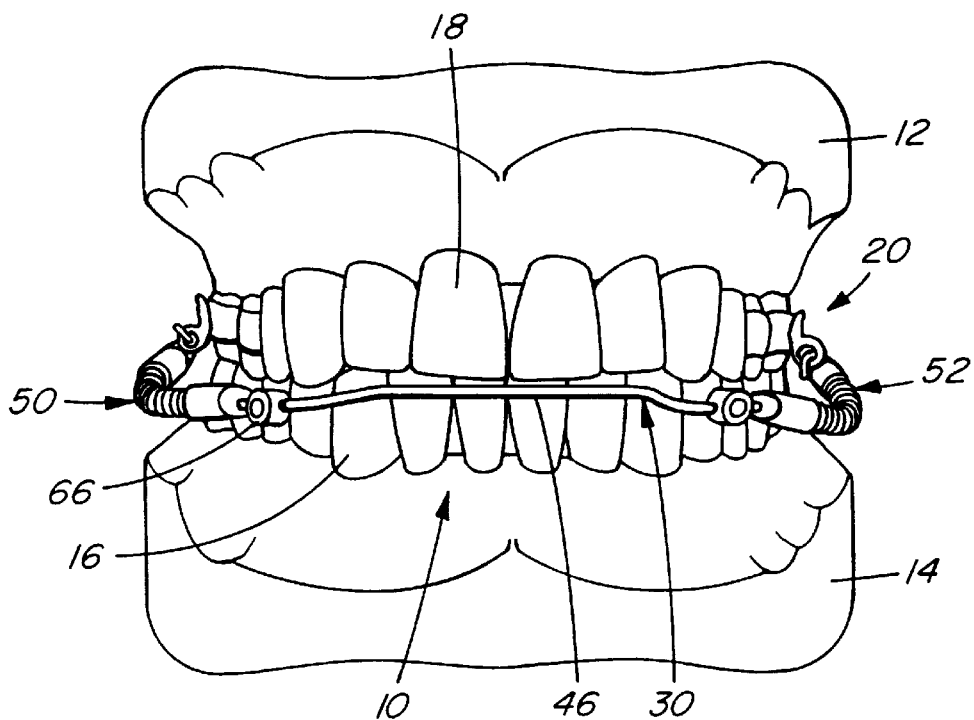
FIG. 2 is an elevational view of the orthodontic appliance as viewed from the front of the patient's mouth.
Figure 3:
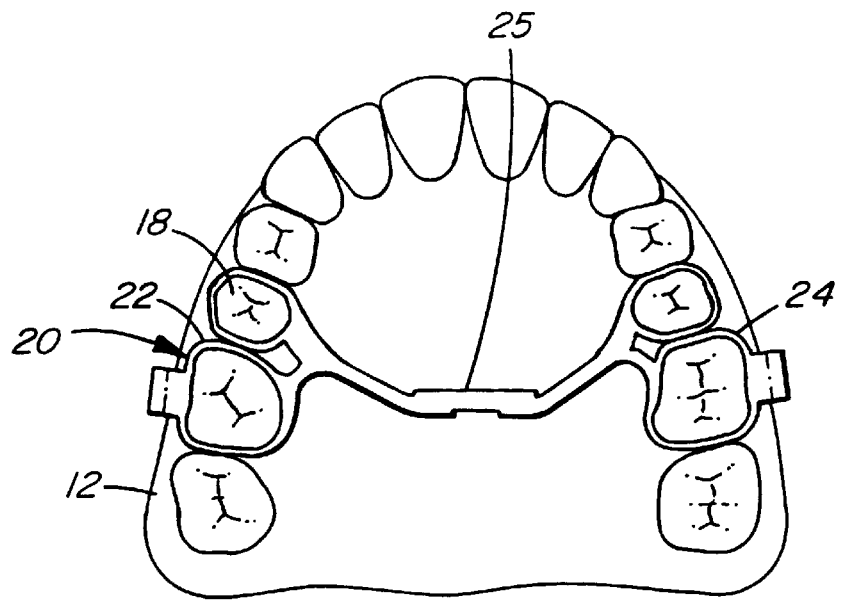
FIG. 3 is a bottom plan view of the upper attachment device thereof, as viewed on the top set of the patient's teeth.
Figure 4:
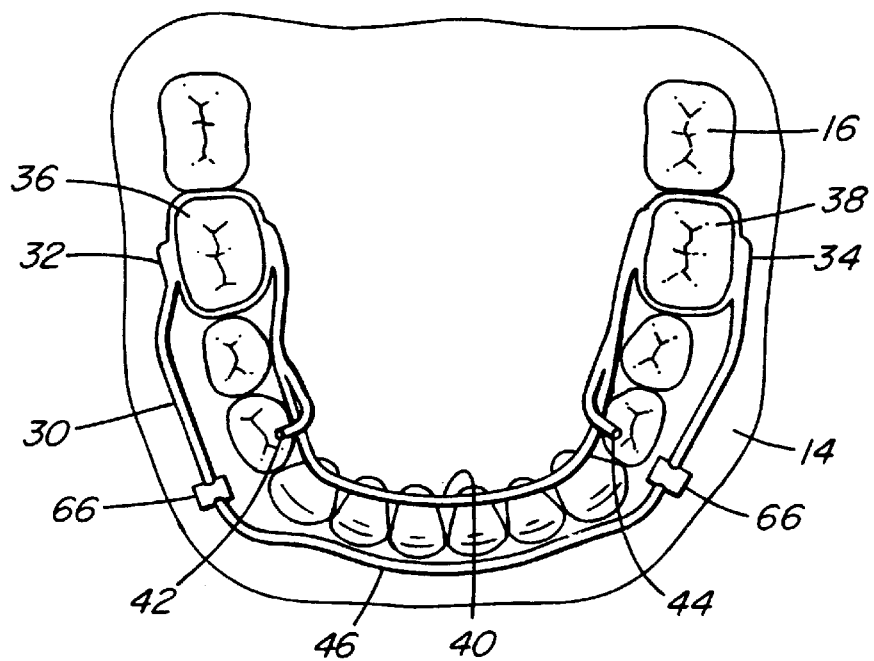
FIG. 4 is a top plan view of the lower attachment device thereof, as viewed on the bottom set of the patient's teeth.
Figure 5:
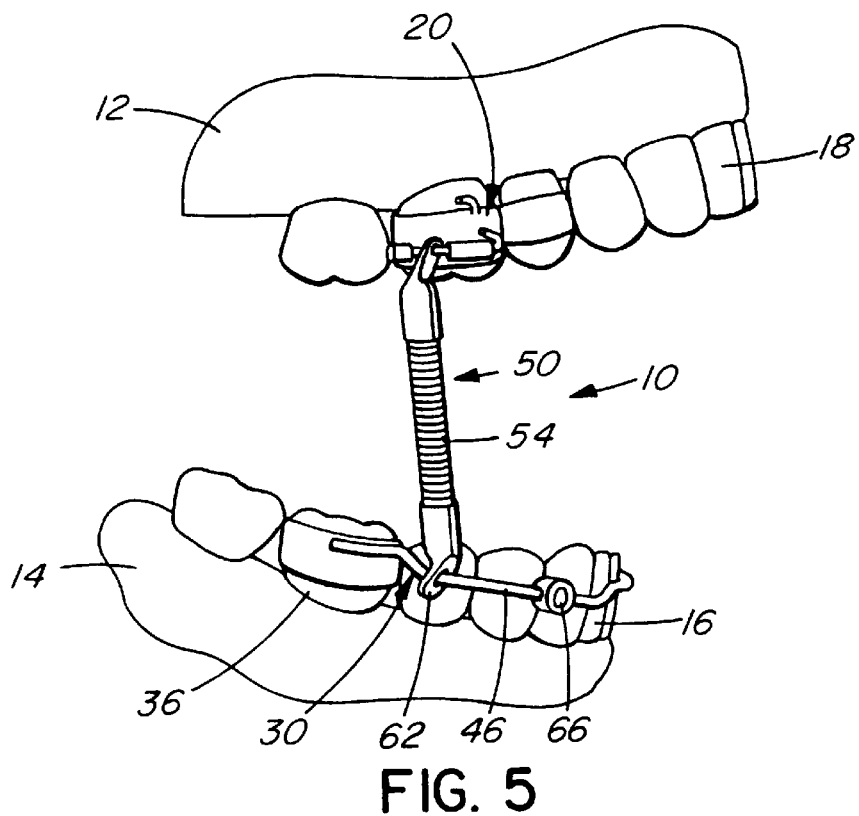
FIG. 5 is a view similar to FIG. 1 with the patient's jaws open.
Figure 6:
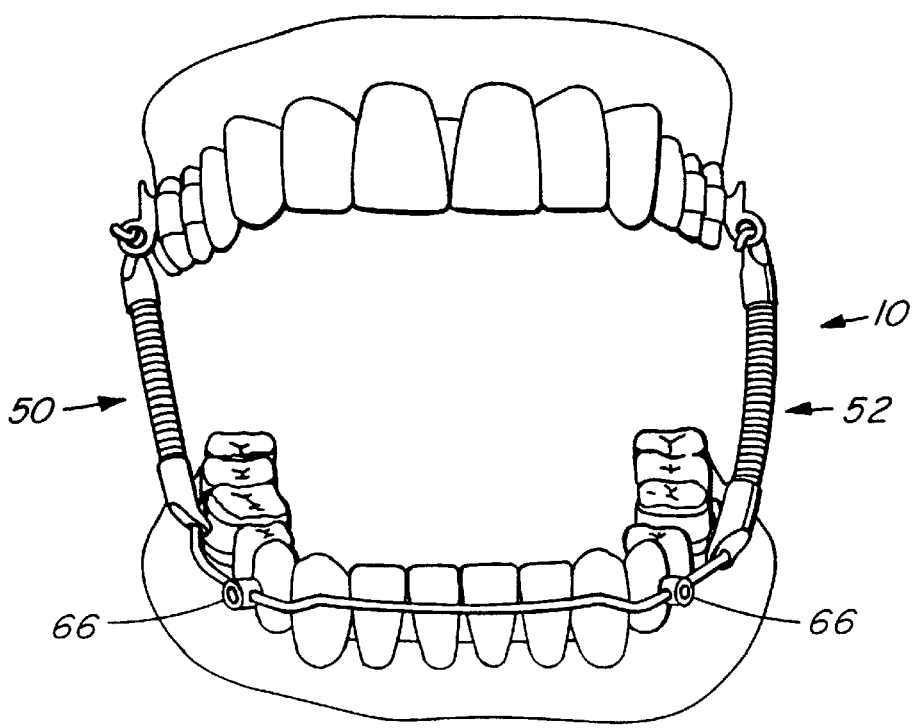
FIG. 6 is a front view thereof.

There is a bite jumping device, in this example a Jasper Jumper 50, interconnecting the upper attachment device and the lower attachment device on one side of the patient's mouth and a similar Jasper Jumper 52 interconnecting the upper attachment device and the lower attachment device on the opposite side of the patient's mouth. Jasper Jumpers are known and, accordingly, these are not described in detail. Each includes an elongated spring 54 which, when bent, biases the lower attachment device forwardly with respect to the upper attachment device. This occurs when the patient's jaws are closed as seen in FIGS. 1 and 2.

In this example each Jasper Jumper has a top eyelet 56 fitted over a wire 58 received in a tube 60 welded to one of the bands 22 or 24. Each has a similar bottom eyelet 62. The labial bow extends slidably through each of the eyelets 62.

There is a stop, in the form of a Gurin lock 66 in this embodiment, on each side of the labial bow to limit forward movement of the Jasper Jumpers. These are known devices and, accordingly, are not described in detail. Each includes a cylindrical member with an aperture, the labial bow extending through the aperture. There is a set screw extending through the cylindrical member to the aperture which can be tightened to lock the device in a desired location on the labial bow. Accordingly, by adjusting the Gurin locks forwardly or rearwardly along the labial bow, the biasing force of the Jasper Jumpers can be reduced or increased as being desirable by the orthodontist. Each eyelet 62 slides forwardly along the labial bow when the patient closes her or his jaws until the eyelet contacts the Gurin lock. Further closing of the jaws causes bending of the springs forcing the upper teeth backwards and the lower teeth forwardly. However opening of the jaws is not impeded since the eyelets can slide rearwardly along the labial bow to a position shown in FIG. 5.

Figure 7:
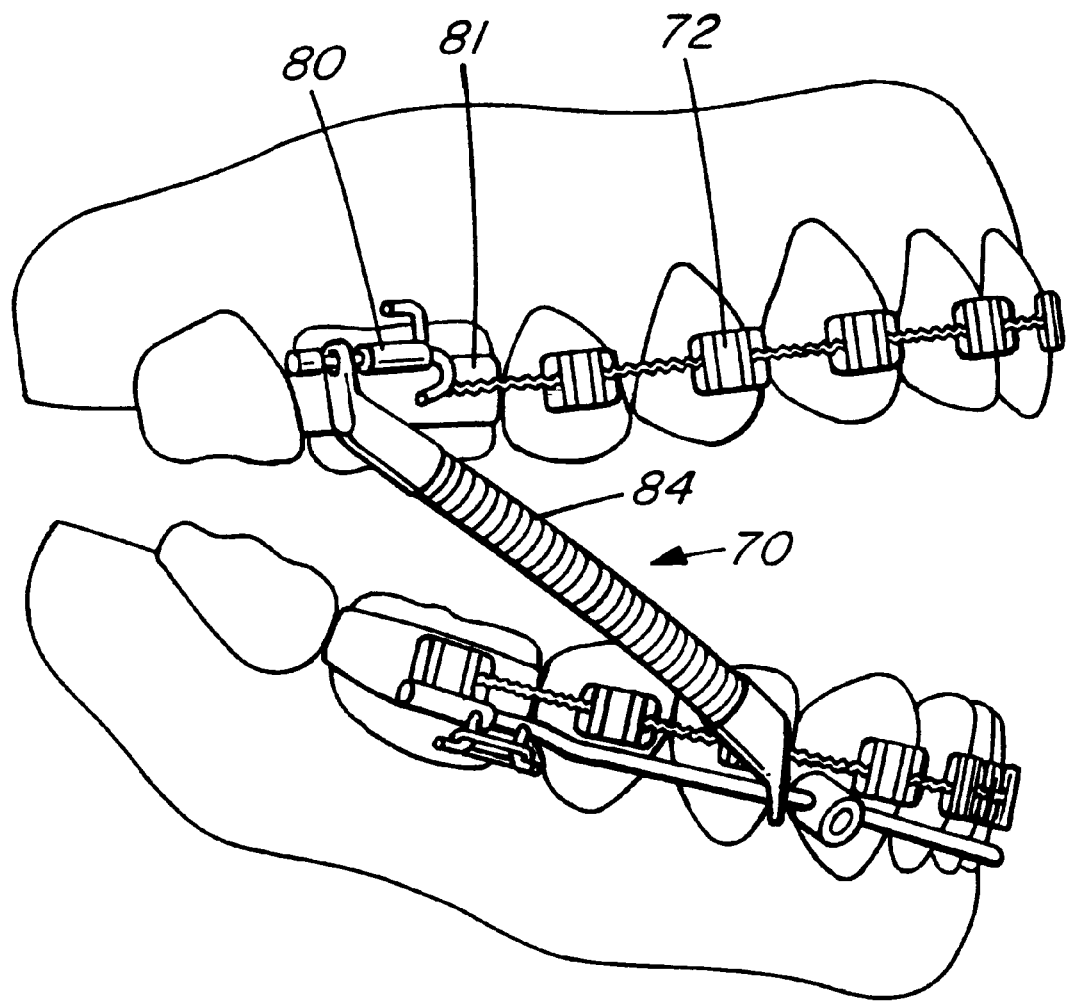
FIG. 7 is a view similar to FIG. 5 of an alternative embodiment of the invention.
Figure 8:
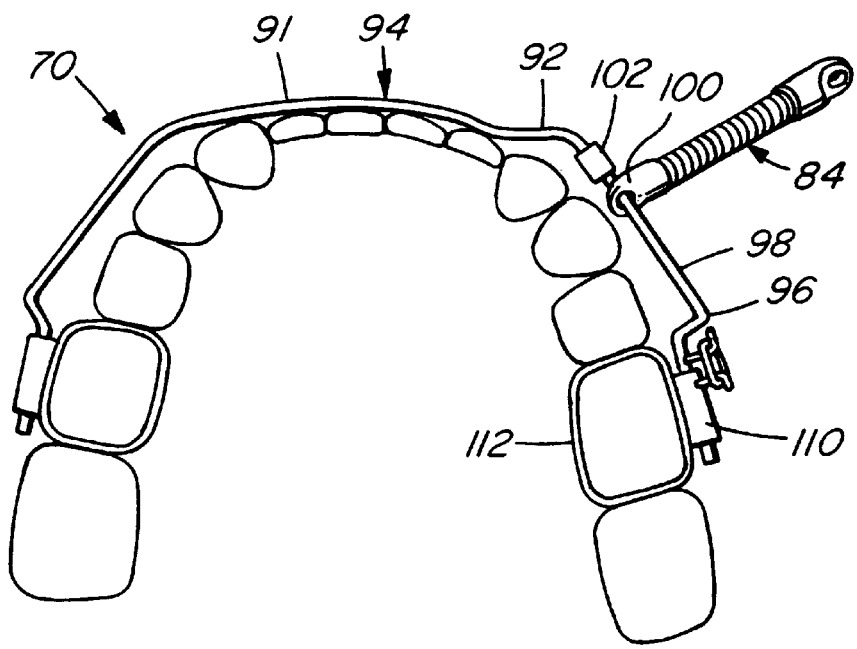
FIG. 8 is a top plan view of the lower attachment device according to the alternative embodiment of the invention.
Figure 9:
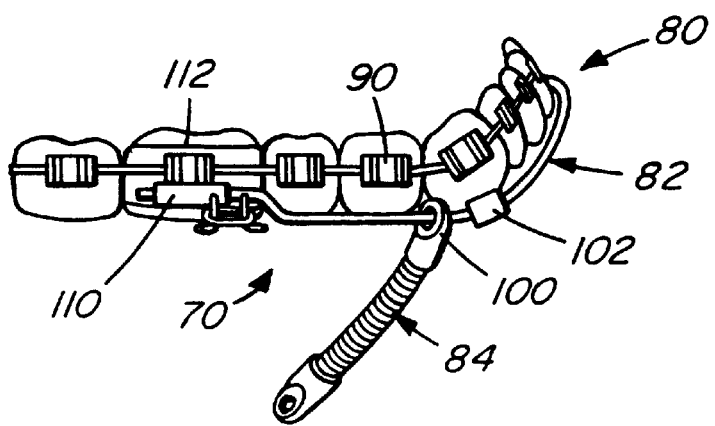
FIG. 9 is a side isometric view thereof.

FIGS. 7, 8 and 9 show an alternative orthodontic appliance 70 which is generally similar to the previous embodiment and, accordingly, is described only with respect to the differences therebetween. This appliance is intended for patients who have permanent dentition and have been fitted with braces 72 including head gear tubes 80 welded to upper molar bands 81 and lip bumper tubes 110 welded to lower molar bands 112. In this case bite jumping device 84 is connected to the upper braces 72 in the conventional manner, similar to the type of connection between the previous jumping devices and the previous upper attachment device.

Only a portion of the device is shown in FIGS. 8 and 9 including lower attachment device 82 and Jasper Jumper 84. This variation is intended for patients who have full braces 90 on permanent lower dentition. In this case there is an anterior or front curvature 91 and a canine or cuspid step out bend 92 on each side thereof on labial bow 94. Likewise there is a molar step out bend 96 on each side located rearwardly of each bend 92. A sliding rail portion 98 of the labial bow extends between the step out bend 92 and the step out bend 96. Eyelet 100 of each of the Jasper Jumpers is slidably received on the sliding rail portion.

A Gurin lock 102 is received on each sliding rail portion forwardly of the Jasper Jumpers. The rear ends of the labial bow are inserted into tube 110 which in turn is welded to molar band 112. A hook in the labial bow is ligated to a hook on the tube by means of a steel ligature wire.

The front curvature 91 contacts the front teeth in the previous embodiments of FIGS. 16, but may clear the front teeth in this embodiment with braces. The bends 92 and 96 on each side of the mouth allow an orthodontist to work on the braces without interference. This provides an auxiliary wire for attachment of the Jasper Jumper which bypasses the lower braces.

If braces are being used to close spaces between the teeth, for example a tooth extraction site, to allow retraction of the front teeth there needs to be a space closure take-up section to allow the labial bow to slide back through the lip bumper tubes 110 on either side so that the anterior curvature is not left too far ahead of the lower front teeth or does not push on the inside of the lower lip. If space is being closed, a Gurin lock with a tie-hook is used as a stop, instead of a soldered hook, to control the size of the space closure take-up section. This allows complete freedom with respect to treatment with braces. It allows the Jasper Jumper to be used with either a non-extraction or extraction orthodontic teclnique. In the past it has generally been used with braces in a non-extraction technique.

The invention has significant advantages over the prior art. First it allows the Jasper Jumper to be used with mixed dentition. It also allows the Jasper Jumper to be used with more patients wearing braces, for example extraction and space closure cases as well as traditional non-extraction cases.

The device is advantageous since it can be used bilaterally or unilaterally. It can also be used "upside-down" in Class III or underbite patients. An upper expansion appliance can be used at the same time. The mixed dentition version can be used with or without braces on the upper front teeth.

It will be understood by someone skilled in the art that many of the details described above are by way of example only and are not intended to limit the scope of the invention which is to be interpreted with reference to the following claims.

What is claimed is:

1. An orthodontic appliance for treating overjet in a patient having a upper jaw, a lower jaw, lower teeth in the lower jaw and upper teeth in the upper jaw which are abnormally forward of the lower teeth, the teeth having lingual sides and labial sides, the appliance comprising:

an upper attachment device configured to be secured to at least one of the upper teeth on each side of the upper jaw;

a lower attachment device having a pair of lower connectors, each said lower connector being configured to be secured to at least one of the lower teeth of the patient on each side of the lower jaw, a rigid, wire-like lingual bow extendable between the lower connectors about the lingual sides of the lower teeth and a rigid, wire-like labial bow extendable between the lower connectors about the labial sides of the lower teeth, said bows being connected to the lower connectors; and a bite jumping device interconnecting each side of the upper attachment device to a corresponding side of the lower attachment device, each said bite jumping device including a first connector for connecting to the upper attachment device, a second connector for connecting to the lower attachment device and a biasing member which biases the lower attachment device forwardly with respect to the upper attachment device.

2. An appliance as claimed in claim 1, wherein the second connector is connected to the labial bow.

3. An appliance as claimed in claim 2, wherein the second connector is adjustably connected to the labial bow, to permit adjustment of the bite jumping device.

4. An appliance as claimed in claim 1, wherein the second connector is slidably connected to the labial bow.

5. An appliance as claimed in claim 4, including a stop on the labial bow to limit forward movement of each said bite jumping device.

6. An appliance as claimed in claim 5, wherein the stop is adjustably movable along the labial bow.

7. An appliance as claimed in claim 6, wherein the stop is a Gurin lock.

8. An appliance as claimed in claim 5, wherein the second connector has an aperture, the labial bow fitting slidably through the aperture in the second connector.

9. An appliance as claimed in claim 1 wherein the bite jumping device is a Jasper Jumper.

10. An appliance as claimed in claim 9, wherein the labial bow and the lingual bow are soldered to the molar bands.

11. An appliance as claimed in claim 10, wherein the wire is generally 0.045" in diameter.

12. An appliance as claimed in claim 1, wherein the upper attachment device includes a palatal expansion appliance.

13. An appliance as claimed in claim 1, wherein each of the lower connectors includes a molar band.

14. An appliance as claimed in claim 1, wherein the upper attachment device includes headgear tubes connected to upper molar bands.

15. An appliance as claimed in claim 1, wherein the lingual bow and the labial bow are of stainless-steel wire.

* * * * *

UNITED STATES PATENT AND TRADEMARK OFFICE
CERTIFICATE OF CORRECTION

PATENT NO. : 6,168,430 B1
APPLICATION NO. : 09/455321
DATED : January 2, 2001
INVENTOR(S) : Duncan Higgins It is certified that error appears in the above-identified patent and that said Letters Patent is hereby corrected as shown below:

Insert
Col. 5, line 10,
10. An appliance as claimed in claim 9, wherein the labial bow and the lingual bow are soldered to molar bands.

Col. 5, line 12,
11. An appliance as claimed in claim 10, wherein each of the wire-like bows is of wire generally 0.045" in diameter.

Signed and Sealed this

Twenty-third Day of October, 2007

JON W. DUDAS
*Director of the United States Patent and Trademark Office*